US00PP37146P2

(12) United States Plant Patent
Bourne

(10) Patent No.: US PP37,146 P2
(45) Date of Patent: Dec. 16, 2025

(54) GRAPEVINE NAMED 'SV36-19-424'

(50) Latin Name: *Vitis vinifera*
Varietal Denomination: SV36-19-424

(71) Applicant: Sunview Vineyards of California, Inc., Delano, CA (US)

(72) Inventor: Timothy F Bourne, Visalia, CA (US)

(73) Assignee: Sunview Vineyards of California, Inc., Delano, CA (US)

( * ) Notice: Subject to any disclaimer, the term of this patent is extended or adjusted under 35 U.S.C. 154(b) by 0 days.

(21) Appl. No.: 18/831,534

(22) Filed: Apr. 7, 2025

(51) Int. Cl.
*A01H 5/08* (2018.01)
*A01H 6/88* (2018.01)

(52) U.S. Cl.
USPC ..... Plt./205

(58) Field of Classification Search
USPC ..... Plt./205
See application file for complete search history.

*Primary Examiner* — Susan McCormick Ewoldt
(74) *Attorney, Agent, or Firm* — Eric C. Cole; Baker Manock & Jensen

(57) ABSTRACT

A new and distinct variety of grapevine plant named 'SV36-19-424' particularly characterized by its very sweet, crisp, red berries with neutral *Vitis vinifera* flavor. Natural cluster size is medium with well-filled, loose clusters. Fruitfulness is high with shoots on spur pruned vines usually producing one flower cluster per shoot.

6 Drawing Sheets

Latin name of the genus and species of the plant claimed: The plant claimed relates to a new and distinct variety of *Vitis vinifera*.

Variety denomination: The plant claimed shall be known as 'SV36-19-424'.

STATEMENT OF ANY FEDERALLY-SPONSORED RESEARCH AND DEVELOPMENT

The present invention is not subject of Federally-sponsored research or development.

BACKGROUND OF THE INVENTION

The present invention comprises a new and distinct cultivar of grapevine botanically known as *Vitis* spp. and hereinafter referred to as grapevine named 'SV36-19-424'. As used herein, 'grapevine' refers to all plant parts including, vines, canes, tendrils, leaves, fruit and roots of 'SV36-19-424'. Grapevine named '36-19-424' is the result of an effort to produce a new, large berried, early-ripening red seedless table grape. This new cultivar originated from a cross conducted in May 2015 near McFarland, California, between female grapevine plant selection 'SV13-2-138' (unpatented) and male parent grapevine plant 'SV28-100-202' (U.S. Plant Pat. No. 34,538). Resultant ovules from the cross were harvested 42 days after pollination and cultured on 'Mccown's Woody Plant Medium'. Subsequently, the resultant embryonic plants were cultured in the same medium in the laboratory under twelve hours of light from standard fluorescent lamps at 27° C. The seedlings from this effort were transplanted to the greenhouse in November of 2015 and grown at 27° C. with 12 hours illumination under high pressure sodium vapor lamps. The seedling population of 193 seedlings was planted in the field in the spring of 2016 near Delano, California. The new grapevine was selected from this seedling population on Jul. 29, 2017. It was then propagated by cuttings and bench grafted to 'Freedom' (unpatented) rootstock in 2018 at a nursery near Delano, California. The present invention has been found to retain its distinctive characteristics through three successive asexual propagations.

Grapevine named 'SV36-19-424' differs from its female parent grapevine 'SV13-2-138' (unpatented) in that 'SV36-19-424' has perfect flowers and red berries while 'SV13-2-138' has pistillate flowers and white berries.

Grapevine named 'SV36-19-424' differs from its male parent, grapevine 'SV28-100-202' (U.S. Plant Pat. No. 34,538) in that 'SV36-19-424' has neutral flavored, red berries while 'SV28-100-202' has red berries with light muscat flavor.

Grapevine 'SV36-19-424' is most similar to commercially available 'Scarlet Royal' (U.S. Plant Pat. No. 16, 229) in that both cultivars have large, red, seedless berries. Grapevine named 'SV36-19-424' differs from 'Scarlet Royal' (U.S. Plant Pat. No. 16,229) by ripening its fruit in mid-August in the Delano, California area as opposed to late August for 'Scarlet Royal'. Further, grapevine named 'SV36-19-424' has no astringency at full ripeness over 20 brix while 'Scarlet Royal' (U.S. Plant Pat. No. 16,229) is typically astringent at full ripeness over 20 brix.

SUMMARY OF THE INVENTION

The following are the most outstanding and distinguishing characteristics of the ripe fruit of this new variety when grown under normal horticultural practices near McFarland, California:

a. Fruit clusters with large, red, seedless berries.
b. Very crisp berry texture.
c. Highly vigorous growth with high fruitfulness.

BRIEF DESCRIPTION OF THE DRAWINGS

This new grapevine is illustrated by the accompanying photographs which show fruit clusters, leaves, canes and tendrils. The colors shown are as true as can be reasonably obtained by conventional photographic procedures. The photographs were taken from the original seedling vine in 2017 and from a vine grafted to 'Freedom' rootstock in 2024.

DETAILED BOTANICAL DESCRIPTION

Figure 1:
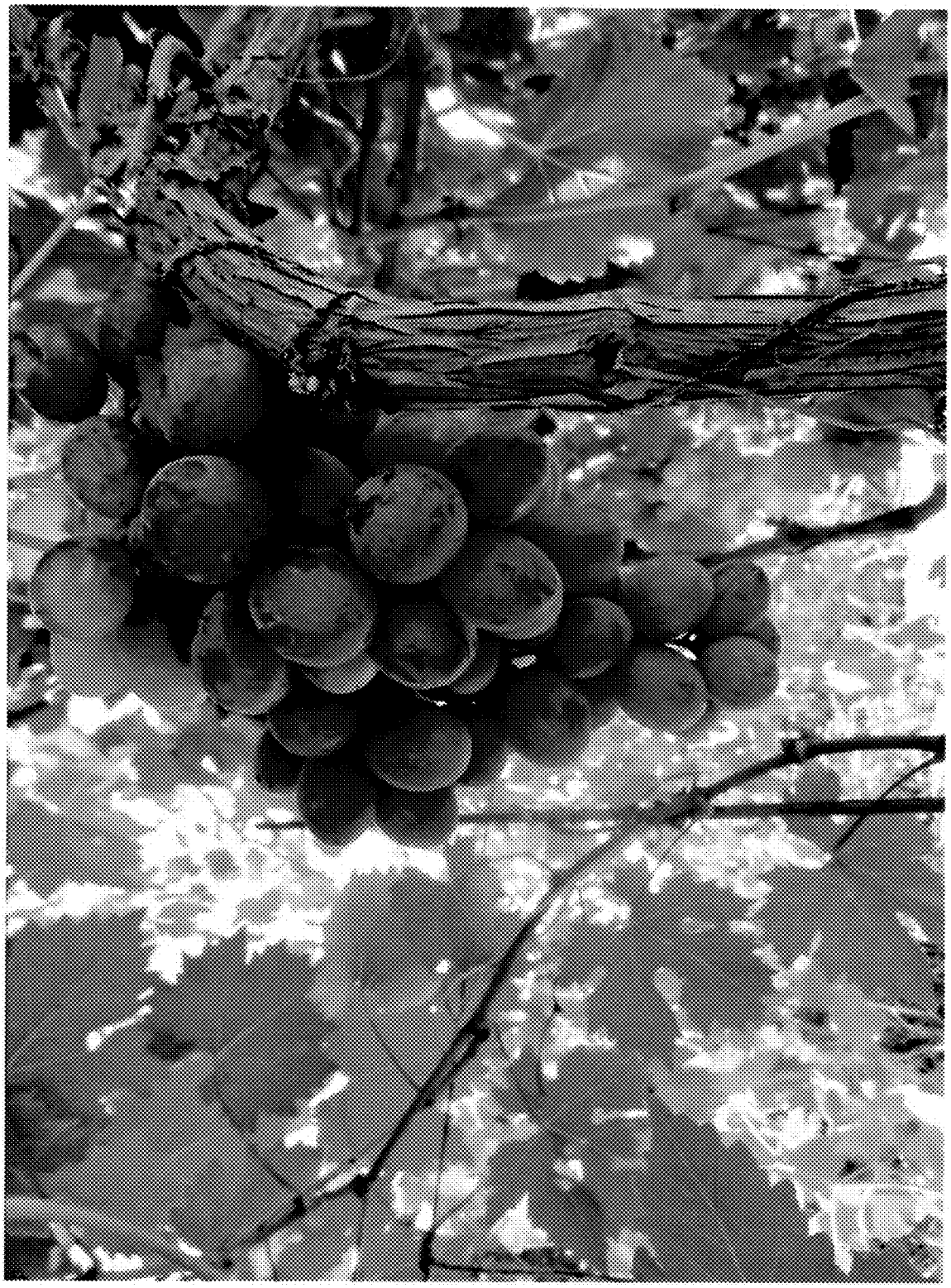
FIG. 1 Fruit cluster on the seedling vine taken in September 2017.
Figure 2:
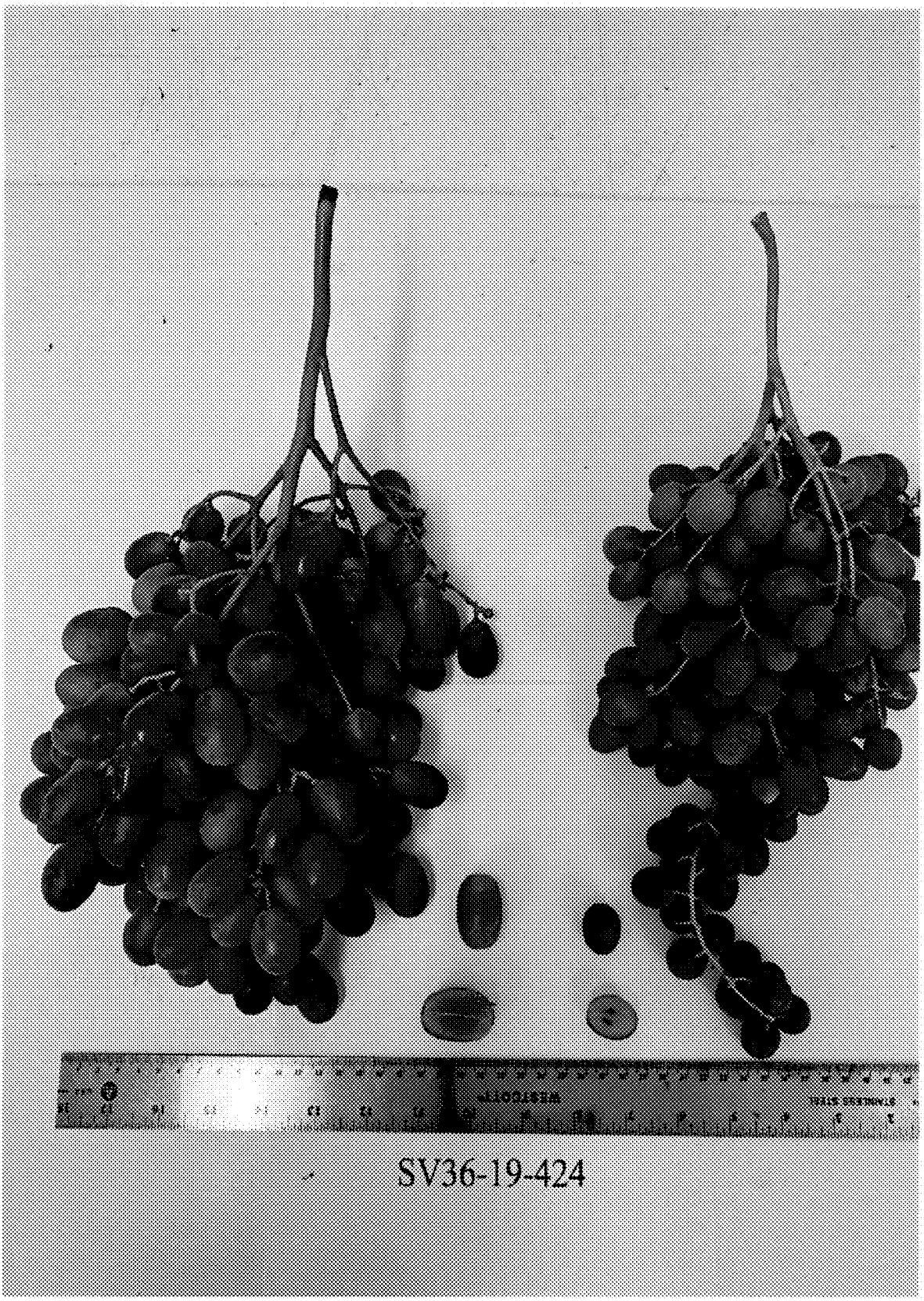
FIG. 2 Fruit cluster (natural at right, from vine treated with exogenous gibberellic acid, at left), taken in September 2022.
Figure 3:
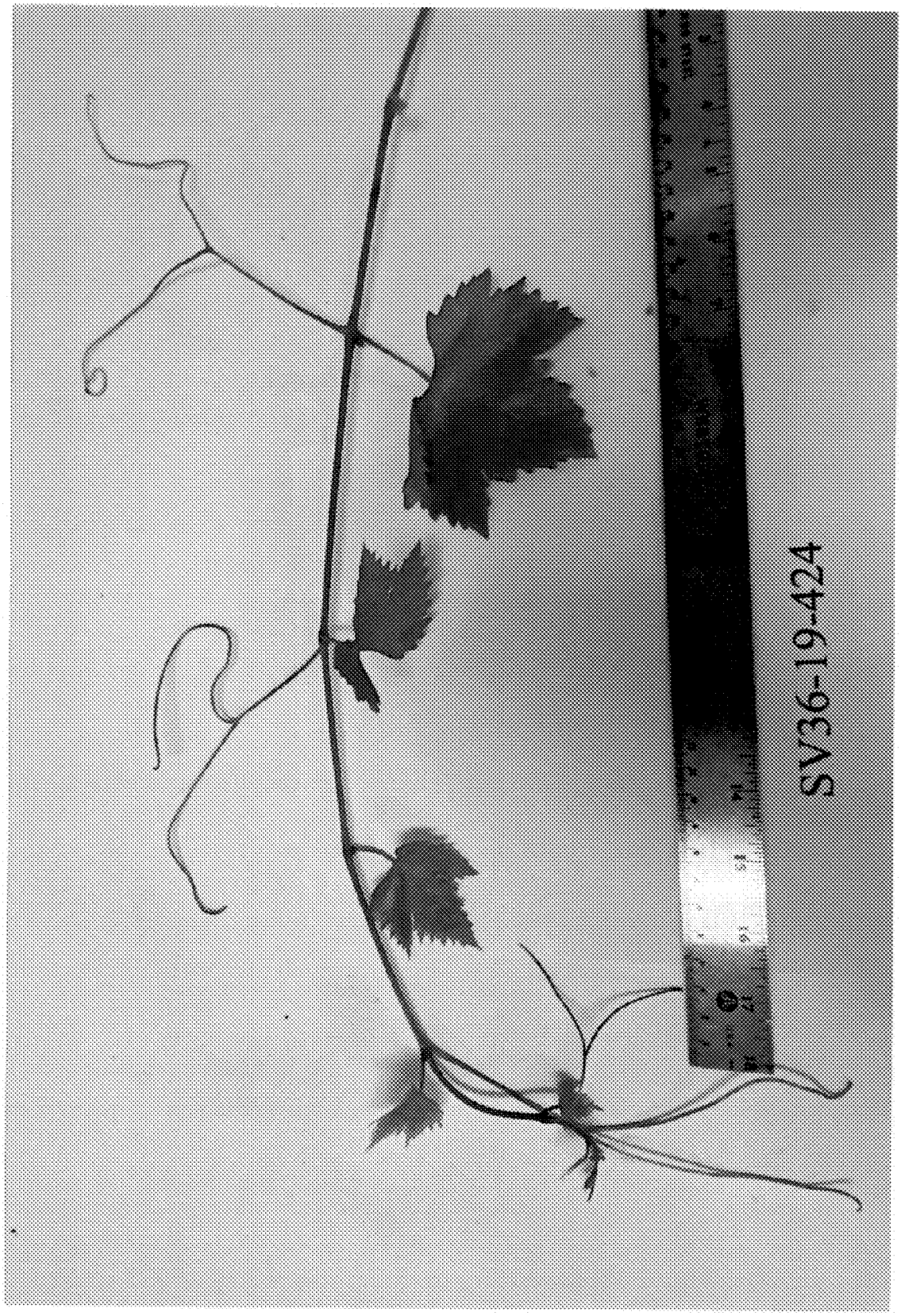
FIG. 3 Shoot with meristem, leaves and tendrils in 2022.
Figure 4:
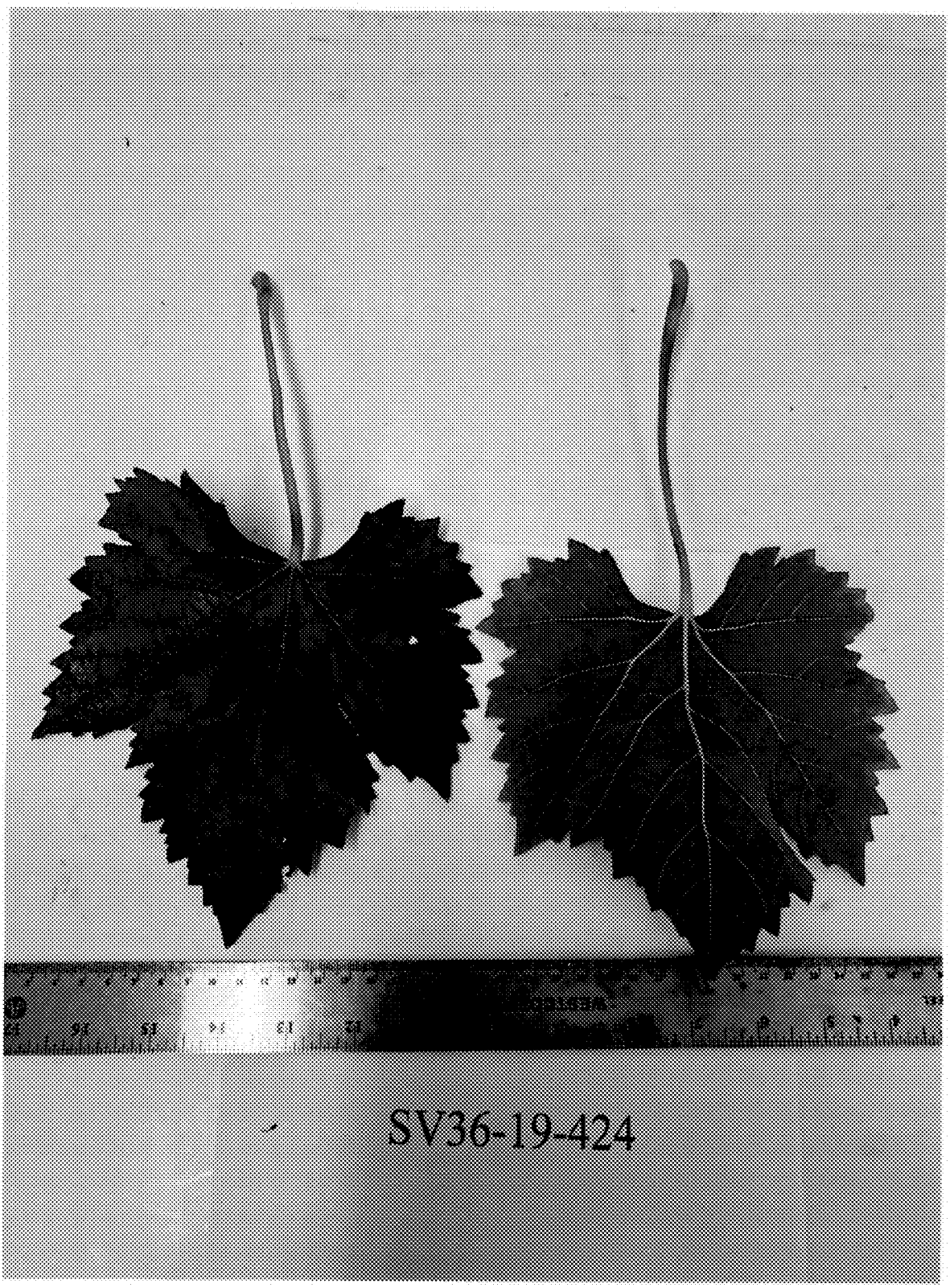
FIG. 4 Leaves, top and bottom view.
Figure 5:
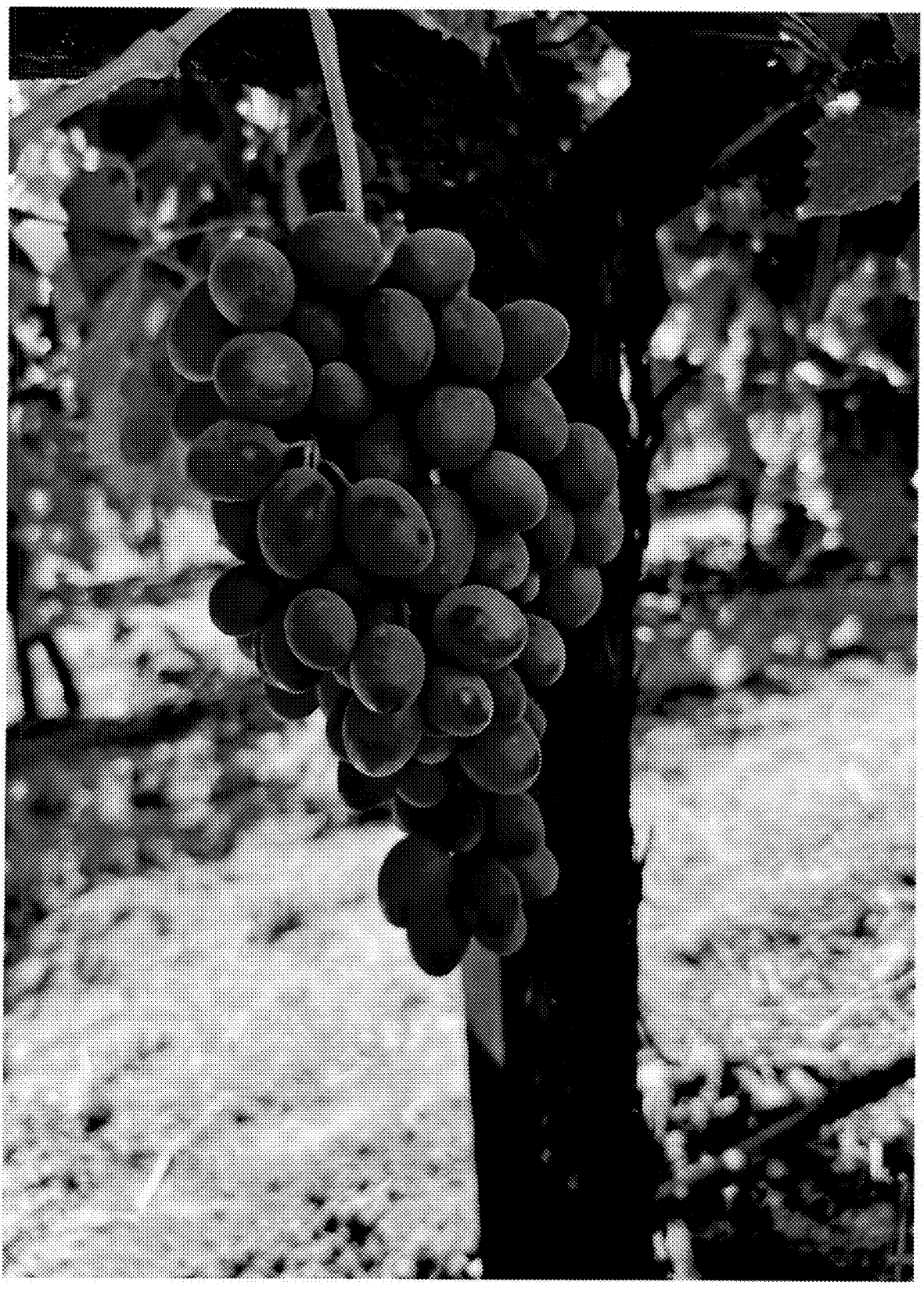
FIG. 5 Fruit on mature vine with no application of gibberellic acid and girdle.
Figure 6:
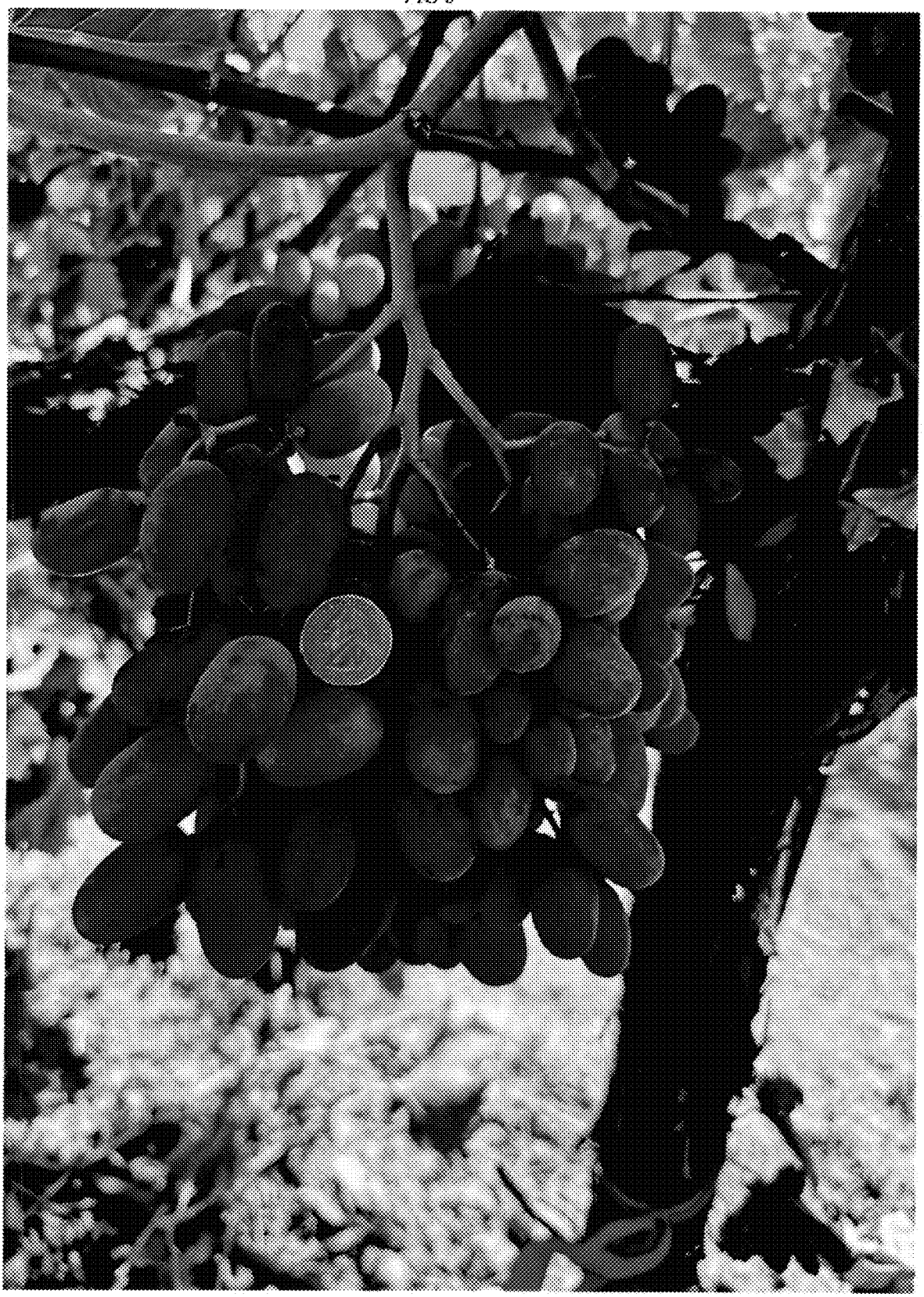
FIG. 6 Fruit on mature vine sprayed with exogenous gibberellic acid and with trunk girdling.

The following detailed description sets forth the distinctive characteristics of 'SV36-19-424'. Descriptions of the new invention apply to vines of 'SV36-19-424' grown on 'Freedom' rootstock at a density of 1,537 vines per hectare grown near McFarland, California in 2023 and 2024. These vines were observed in the immediate year following planting and in the following year of full production having been planted in 2018. These descriptions are believed to apply generally to the new variety grown under similar circumstances elsewhere. Variation due to soil and climatic conditions in other locations may be seen. References to color correspond to The Royal Horticultural Society's Colour Chart, The Royal Horticultural Society, London, United Kingdom (copyright 2001). Descriptors used herein conform to those set forth by the International Board for Plant Genetic Resources Institute Grape Descriptors (*Vitis* spp.) of 1983 and/or 1997 which were developed in collaboration with the Office International de la Vigne et du Vin (OIV) and the International Union for the Protection of New Varieties of Plants (UPOV) and published in *Descriptors for Grapevine* (*Vitis* spp.) (Anonymous, International Plant Genetic Resources Institute, 1997, ISBN 92-9043-352-3).

Classification:

*Family*.—Vitaceae.

*Botanical name*.—*Vitis vinifera*.

*Variety name*.—'SV36-19-424'.

Plant:

*Vigor*.—Vines spur-pruned and shoot thinned to 32 shoots average 183.13 cm of growth per cane.

*Density of foliage*.—Medium.

*Productivity*.—High, up to 42,664 kilograms per hectare.

*Hardiness*.—Observed to 0° C.

*Rootstock*.—'Freedom' (unpatented).

Trunk:

*Shape*.—Broadly elliptical.

*Straps*.—Long, split.

*Surface texture*.—Shaggy, rough.

*Trunk circumference*.—20.6 cm, measured at 1 meter height above soil.

*Inner bark color*.—RHS greyed-orange group 165A.

*Outer bark color*.—RHS brown group N200C.

Mature leaves:

*Average blade length*.—15.0 cm.

*Average blade width*.—18.3 cm.

*Size of blade*.—Large.

*Shape*.—Pentagonal.

*Number of lobes*.—5.

*Anthocyanin coloration of main veins on the upper side of the blade*.—Absent.

*Color of main veins, upper surface of leaves*.—RHS yellow-green group 146A.

*Color of main veins, lower surface of leaves*.—RHS yellow-green group 150D.

*Venation pattern*.—Pentagonal with 5 main veins.

*Mature leaf profile*.—Undulating.

*Blistering* (*upper surface*).—Absent.

*Leaf blade tip*.—Curved upwards.

*Margins*.—Lobed, doubly serrate.

*Apex*.—Broadly acute.

*Bases*.—Sagittate.

*Thickness*.—Medium.

*Undulation of blade between main and lateral veins*.—Slight.

*Shape of teeth*.—Both sides convex.

*Length of teeth*.—8.7 mm.

*Width of teeth*.—10.6 mm.

*Ratio length/width of teeth*.—8.7:10.6.

*General shape of petiole sinus*.—Closed.

*Tooth at petiole sinus*.—Absent.

*Petiole sinus limited by veins*.—Absent.

*Shape of upper lateral sinus*.—Slightly overlapping.

*Prostrate hairs between veins* (*lower surface*).—Low density.

*Erect hairs between veins* (*lower surface*).—Medium density.

*Prostrate hairs on main veins* (*lower surface*).—Low density.

*Density of erect hairs on main veins* (*lower surface*).—Absent.

*Prostrate hairs on main veins* (*upper surface*).—Low density.

*Upper surface*.—Summer color: RHS yellow-green group 147A. Surface texture: Smooth. Surface appearance: Dull. Goffering of blade: Absent.

*Lower surface*.—Summer color: RHS yellow-green group 146B. Anthocyanin coloration of main veins on lower leaf surface: Absent. Anthocyanin coloration on laterals: Absent. Glossiness: Low. Pubescence: Absent. Surface texture: Rough. Surface appearance: Dull.

*Petiole*.—Length: 13.1 cm. Length of petiole compared to middle vein: About equal. Density of prostrate hairs: Absent. Density of erect hairs: Absent. Shape of base of petiole sinus: Sagittate. Color: In shade: RHS yellow-green group 144B In sun: RHS yellow-green group 144A.

Tendrils:

*Number & pattern*.—Bifurcated and trifurcated; Continuous after 5th node.

*Length*.—29.5 cm.

*Diameter*.—3.3 mm.

*Texture*.—Smooth.

*Color*.—RHS yellow-green group 150C.

Growing tips (young shoot):

*Pubescence*.—Abundant, prostrate.

*Color*.—RHS yellow-green group N144C.

*Anthocyanins*.—Absent.

*Shape*.—Rounded.

*Apex*.—Fully open.

*Shoot attitude*.—Semi-erect.

Green summer shoots:

*Internode color upper surface*.—RHS greyed-orange group 177A.

*Internode color lower surface*.—RHS yellow-green group 144A.

*Node color upper surface*.—RHS greyed-orange 177A.

*Node color lower surface*.—RHS yellow-green group 144A.

*Density of erect hairs on internodes*.—Absent.

Woody shoot:

*Canes*.—Shape: Elliptical. Internode length: 12.12 cm. Internode diameter: 0.94 cm. Width at node: 1.46 cm. Main color: RHS Greyed-Orange group N172A.

*Laterals*.—Shape: Elliptical. Number: 1-2. Length: 27.4 cm. Diameter: 5.0 mm. Internode length: 4.3 cm. Color: RHS yellow-green group 144B.

*Buds*.—Shape: Conical. Length: 5.3 mm. Width: 4 mm. Height: 4.8 mm. Color: RHS Brown group 200A. Texture: Smooth.

Flowers:

*Flower sex*.—Perfect.

*Position of first flowering nodes*.—$5^{th.}$

*Number of inflorescences per shoot*.—1.

*Flower cluster width*.—12.6 cm.

*Flower cluster length*.—34 cm.

*Cluster stem color*.—RHS Yellow-Green group 144B.

*Calyptra color*.—RHS yellow-green group 144C.

*Ovary length*.—2 mm.

*Ovary width*.—1.7 mm.

*Ovary color*.—RHS yellow-green group 144A.

*Filament length*.—1.9 mm.

*Filament color*.—Translucent, absence of pigmentation.

*Anther length*.—1 mm.

*Anther color*.—RHS greyed-orange group 165B.

*Date of full bloom*.—May 6, 2024.

Fruit:

*Ripening period*.—Early mid-season, Delano, California.

*Date of ripening*.—Aug. 8, 2022, Delano, California.

*Use*.—Fresh market.

*Keeping quality*.—Very good. No decay after 30 days of cold storage at 0.56 C.

*Shipping quality*.—Good. There was no detached berries found in a 8.6 kg box of fruit test-shipped by truck for 4 hours at 0.56 C.

*Solids-sugar*.—High, about 20 brix at full maturity.

*Refractometer test*.—20 brix. Natural, without gibberellic acid treatment: 19.5. With gibberellic acid treatment: 20.5.

*Bunch*.—Size: Large. Length (peduncle excluded): Natural, without gibberellic acid treatment: 21.76 cm. With gibberellic acid treatment: 23.92 cm. Width: Natural, without gibberellic acid treatment: 17.86 cm. With gibberellic acid treatment: 21.56 cm. Weight: Natural, without gibberellic acid treatment: 809 g. With gibberellic acid treatment: 1189 g. Density: Well-filled, but loose. Number of berries: Natural, without gibberellic acid treatment: 133. With gibberellic acid treatment: 135. Form: Conical.

*Peduncle*.—Length: 6.8 cm. Lignification: 7.03 cm. Color: RHS Yellow-Green group 144B.

*Berry*.—Size: Large. Uniformity of size: Uniform. Weight: Natural, without gibberellic acid treatment: 6.8 g. With gibberellic acid treatment: 8.4 g. Shape: Natural, without gibberellic acid treatment: Ovate. With gibberellic acid treatment: Oblong. Presence of seeds: Present, small, soft seeds, 4-5 mm in length. Cross section: Circular. Dimensions: Longitudinal axis: Natural, without gibberellic acid treatment: 2.96 cm. With gibberellic acid treatment: 3.46 cm. Horizontal axis: Natural, without gibberellic acid treatment: 2.32 cm. With gibberellic acid treatment: 2.32 cm. Skin color (without bloom): RHS Greyed-Purple group N187A. Coloration of flesh: RHS Yellow-Green group 145D. Juiciness of flesh: Juicy. Berry firmness: Firm. Particular flavor: Typical vinifera, Good sugar. Bloom (cuticular wax): Medium. Pedicel length: Natural, without gibberellic acid treatment: 0.82 cm. With gibberellic acid treatment: 0.98 cm. Berry separation from pedicel: With difficulty.

*Skin*.—Thickness: Medium. Texture: Tender, crip. Reticulation: Absent. Roughness: Smooth. Tenacity: Tenacious to berry flesh. Tendency to crack: None.

Having thus described and illustrated our new variety of grapevine, I claim:

1. A new and distinct variety of grapevine plant named 'SV36-19-424', substantially as illustrated and described herein.

* * * * *